United States Patent [19]
Snell

[11] Patent Number: 5,792,204
[45] Date of Patent: Aug. 11, 1998

[54] METHODS AND APPARATUS FOR CONTROLLING AN IMPLANTABLE DEVICE PROGRAMMER USING VOICE COMMANDS

[75] Inventor: Jeffery D. Snell, Oak Park, Calif.

[73] Assignee: Pacesetter, INc., Sylmar, Calif.

[21] Appl. No.: 664,070

[22] Filed: Jun. 13, 1996

Related U.S. Application Data

[60] Provisional application No. 60/017,228, May 8, 1996.

[51] Int. Cl.⁶ ........................................ A61N 1/08
[52] U.S. Cl. ........................................ 607/32
[58] Field of Search ........................ 607/30, 31, 32, 607/60

[56] References Cited

U.S. PATENT DOCUMENTS

| 4,006,309 | 2/1977 | Brickerd, Jr. | 361/157 |
| 5,117,460 | 5/1992 | Berry et al. | 381/41 |
| 5,433,736 | 7/1995 | Nilsson | 607/32 |

Primary Examiner—William E. Kamm
Assistant Examiner—Scott M. Getzow

[57] ABSTRACT

Methods and apparatus for controlling an implantable medical device, such as an implantable cardiac stimulating device, using voice commands are provided. A voice command given by a user is converted into digital data. The digital data are processed in order to recognize the voice command. Once the voice command is recognized, it is telemetered to the implantable device. In a preferred embodiment, the voice command must be confirmed by the user before it is executed.

22 Claims, 4 Drawing Sheets

METHODS AND APPARATUS FOR CONTROLLING AN IMPLANTABLE DEVICE PROGRAMMER USING VOICE COMMANDS

This application claims the benefit of U.S. Provisional Application No. 60/017,228, filed May 8, 1996.

BACKGROUND OF THE INVENTION

This invention relates to methods and apparatus for controlling an implantable medical device, such as an implantable cardiac stimulating device. In particular, this invention relates to methods and apparatus for controlling an implantable medical device using voice commands.

Implantable cardiac stimulating devices which provide electrical stimulation in response to a variety of pathological cardiac arrhythmias are known. Some implantable cardiac stimulating devices provide "tiered therapy," in which the type of electrical stimulation provided is determined in accordance with the severity of the arrhythmia, with more aggressive therapies being applied in response to more severe arrhythmias. For example, such devices may respond to relatively less severe forms of tachycardia by delivering antitachycardia pacing pulses of about 25 μjoules to about 30 μjoules in a sequence known to interrupt such episodes. In response to relatively more severe forms of tachycardia, the implantable cardiac stimulating device may deliver a low energy cardioversion shock on the order of about 2 joules to about 5 joules, either in combination with, or as an alternative to, antitachycardia pacing pulses. In response to an occurrence of an even more severe arrhythmia, for example, ventricular fibrillation, the implantable cardiac stimulating device may deliver a high energy defibrillation shock on the order of about 10 joules to about 40 joules.

Implantable cardiac stimulating devices which provide pacing pulses to cardiac tissue to maintain a heart rate at a physiologically acceptable rate (i.e., to provide "bradycardia pacing support") are also known. Bradycardia pacing support may be provided by a dedicated pacemaker, or by a device that is also capable of providing other forms of therapy, such as tiered therapy.

Implantable cardiac stimulating devices typically contain a microprocessor to control the administration of the various pacing therapies and cardioversion and defibrillation shocks. With each beat of the patient's heart, the implantable cardiac stimulating device makes decisions as to whether electrical stimulation is necessary and what type of electrical stimulation to apply. This decision requires analysis of medical data (such as physiological and electrophysiological data) gathered in real-time from the patient's heart and compared against standards contained in a computer program executed by the microprocessor.

The computer program carries out instructions given by the patient's physician. These instructions are tailored by the physician for a particular patient based upon the physician's training and experience. Thus, the computer program is not an unalterable set of instructions burned into the implantable cardiac stimulating device at the time of manufacture.

Many implantable cardiac stimulating devices serve the patient for years. During these years of service, important changes occur. These include changes in characteristics of the patient's health problem, changes in the characteristics of the tissue adjacent the implantable cardiac stimulating device, changes in the characteristics of the implantable cardiac stimulating device such as remaining strength of the implanted battery, and changes in medical knowledge about cardiac arrhythmias and the preferred therapies for such arrhythmias.

In order to analyze the status of the implantable cardiac stimulating device and receive information gathered from the patient's heart by the device, a specialized computer called an programmer-analyzer, which is able to communicate telemetrically with the device, is used. The implantable cardiac stimulating device is capable of receiving and transmitting information from its implanted location to a telemetry head placed on or near the surface of the patient's body.

By using the programmer-analyzer the physician is, for example, able to monitor the performance of the patient's heart, the implantable cardiac device's recognition and characterization of the sinus rhythm, the implantable cardiac device's choice and timing of therapeutic electrical stimulation, and the reaction of the patient's heart to the therapy. The process of evaluating the performance of the implanted cardiac stimulating device also may involve analysis of atrial intracardiac electrograms (AIEGMs) and ventricular intracardiac electrograms (VIEGMs). After checking these and other parameters, the physician can reset the programming parameters of the implantable cardiac stimulating device.

The programmer-analyzer is used extensively during the procedure in which the implantable cardiac stimulating device is implanted. For example, during the implantation procedure the physician may utilize the programmer-analyzer to test the position of the pacing lead(s) within the patient's heart, to set the threshold of electrical energy delivered to the patient's heart by the device, and to monitor the electrical signals produced by the patient's heart.

In order to control previously known programmer-analyzers, a manually operated input device such as a keypad, mouse, or light-pen has been used. These types of input devices usually require the user to manipulate the device with the user's hands (e.g., pressing a key on a keypad). During procedures in which the programmer-analyzer is used, the physician often is attending to the patient and is thus unable to easily enter commands into the programmer. In order to enter a command, it is common for a physician to communicate the command to an assistant who then manually enters it into the programmer-analyzer.

One example of a situation in which an assistant is used to enter commands is during the implantation procedure. As stated above, it is common for the physician to test the position of the lead(s) of the device by measuring their impedance during the implantation procedure. With previously known programmer-analyzers, measurement of the impedance has been accomplished by having an assistant manually enter the command to measure the lead impedance into the programmer-analyzer via a keypad or similar device. The physician would, for example, move the lead within the patient's heart and then indicate to an assistant to enter the measure command. The assistant would then enter the command and give the results to the physician. Thus, taking a simple lead impedance measurement during the implantation procedure using a conventional programmer-analyzer requires a coordinated effort between two medical practitioners.

In situations where an assistant is not used, the physician may have to interrupt the procedure that he or she is carrying out in order to enter commands into the programmer-analyzer. In such situations, the physician may be forced to alternate between using his or her hands to perform a medical procedure and to manipulate the programmer-analyzer.

In view of these shortcomings, it would be advantageous to provide a programmer-analyzer in which commands could be entered without having to manually operate an input device.

SUMMARY OF THE INVENTION

The present invention provides an implantable medical device programmer-analyzer which is controlled using voice commands. In accordance with the present invention, the programmer-analyzer preferably recognizes voice commands and uses the commands to control an implantable medical device, such as an implantable cardiac stimulating device, via a telemetry circuit. In order to accomplish this, the following steps preferably are carried out. First, a voice command provided by a user is converted into digital data. The digital data are then processed in order to determine if the digital data correspond to any one of a plurality of recognized implantable medical device commands. Once a command has been recognized, the command may be used, for example, to control the implantable medical device using the telemetry circuit.

In a preferred embodiment, the user must confirm the command before it is telemetered to the implantable cardiac stimulating device. In order to accomplish this, the command preferably is communicated back to the user after it is recognized by the programmer. The user then provides either a positive response which causes the command to be executed, or alternatively, a negative response which causes the command to be disregarded. In this manner inappropriate commands are not inadvertently transmitted to the implantable medical device.

In another preferred embodiment, an indicator word is used to alert the programmer that a command will follow. The programmer preferably waits until the indicator word is given by the user before it attempts to recognize the voice commands as implantable medical device commands. This eases the processing burden on the programmer.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

Figure 1:
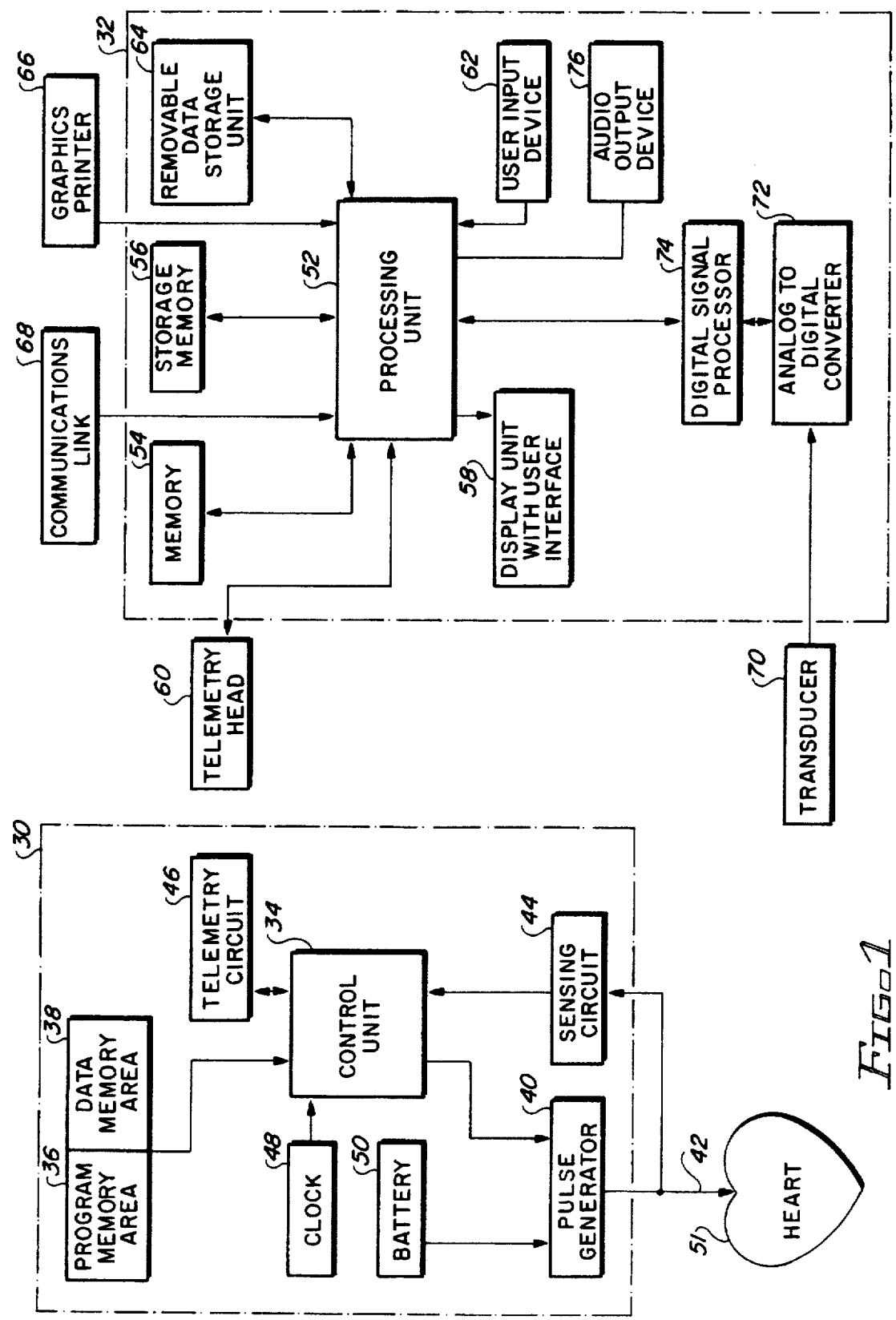
FIG. 1 is a block diagram of an implantable cardiac stimulating device and a programmer-analyzer constructed in accordance with the present invention.

An implantable cardiac stimulating device 30 and an implantable device programmer 32 constructed in accordance with this invention are shown in FIG. 1. Although, the programmer 30 is shown controlling the implantable cardiac stimulating device 32 in FIG. 1, the programmer 32 may, in general, be used to control any type of implantable medical device, including a monitoring device.

As shown in FIG. 1, the implantable cardiac stimulating device 30 may operate as a dedicated pacemaker, a cardioverter/defibrillator, or a combination of both. The operation of the implantable cardiac stimulating device 30 is controlled by a control unit 34, which preferably contains control circuitry (not shown) and a microprocessor (not shown) for executing control program instructions that are stored in a program memory area 36. A data memory area 38 is provided for storing medical data (i.e., data collected by the implantable cardiac stimulating device 30 from the patient's heart 51). The program memory area 36 and the data memory area 38 may be memory blocks in a single memory unit or may be two separate memory circuits.

The control unit 34 also includes self-diagnostic circuitry (not shown) for monitoring the operational characteristics of the implantable medical device 30, such characteristics including, but not being limited to, battery voltage, battery current, internal battery impedance, and lead impedance. A preferred example of self-diagnostic circuitry is disclosed in commonly-assigned U.S. Pat. No. 5,507,786, issued Apr. 16, 1996, entitled "System and Method for Measuring and Storing Parametric Data Pertaining to operating Characteristics of an Implantable Medical Device," which is hereby incorporated by reference. The operational characteristics may be monitored by the implantable medical device 30 between or during office visits.

A pulse generator 40 is connected to the patient's heart 51 via at least one lead 42. The lead 42 is used for cardiac data acquisition (i.e., sensing the patient's IEGM), as well as for the delivery of therapeutic pulses. Therapeutic pulses may be pacing pulses delivered to maintain a normal heart rate, or higher energy shocks delivered to end an occurrence of tachycardia or fibrillation. The pulse generator 40 generates therapeutic pulses administered through the lead 42 to the patient's heart 51 under the direction of the control unit 34. A sensing circuit 44 converts analog data acquired by the lead 42 into digital form which is capable of being analyzed by the control unit 34, stored in the data memory area 38, and transmitted to the programmer 32 by telemetry through an internal telemetry circuit 46. A real time clock 48 is used to provide timing for monitoring cardiac events and for timing the application of therapeutic pulses by the pulse generator 40. A battery 50 supplies the necessary power to the pulse generator 40 (and to other components of the implantable medical device 30 through connections that are not shown).

In a preferred embodiment, the programmer 32 is a pen-based tablet computer such as the one disclosed in commonly-assigned U.S. patent application Ser. No. 08/510, 367, filed Aug. 2, 1995, entitled "Improved User Interface for an Implantable Medical Device Using an Integrated Digitizer Display Screen," which is hereby incorporated by reference. Other types of programmers may also be used without departing from the scope of the invention.

The programmer 32 is controlled by a processing unit 52, which is preferably microprocessor-based. A programmer memory 54 (preferably random access memory) is used by the processing unit 52 for software operation and data processing, while a storage memory 56 is used for long term data storage. The storage memory 56 may be any type of memory suitable for long term data storage including a hard disk drive, flash memory, or a rewritable optical disk.

The programmer 32 is also provided with a graphical display unit 58. The display unit 58 is used to display medical data obtained through the implantable medical device 30, as well as various other data gathered from the patient.

An external telemetry head 60 is used to communicate with the implantable medical device 30 through telemetry.

The programmer 32 is able to send various types of information and instructions to the implantable cardiac stimulating device 30 via the telemetry head 60. For example, the programmer 32 is able to communicate instructions to the implantable cardiac stimulating device 30 which cause the control unit 34 of the device 30 to execute specific programs. These programs may, for example, measure the impedance of the lead 42, interrogate the program settings of the device 30, check the status of the battery 50, or obtain an AIEGM or VIEGM from the patient's heart. The results provided by the various programs carried out by the implantable cardiac stimulating device 30 may then be telemetered back to the programmer 32 to be reviewed by a physician.

The programmer 32 may also program the device 30 via the telemetry head. Program instructions stored within the device 30 may be altered or replaced with new program instructions via the telemetry head 60. Data to be used by programs may also be entered into the device 30 via the telemetry head 60. In addition, the patient's historical medical data may also be telemetered to the device 30 and stored within the device. A preferred system for storing historical medical data in the implantable device 30 is disclosed in commonly-assigned U.S. patent application Ser. No. 510, 369, filed Aug. 2, 1995, entitled "A System and Method for Storing and Displaying Historical Medical Data Measured by an Implantable Medical Device," which is hereby incorporated by reference.

The user is able to interact with the programmer 32 through a user input device 62, which may, for example, be a keyboard, a pen, or a mouse. The use of such an input device to enter information is referred to herein as "manually" entering data.

A removable data storage unit 64, such as a floppy disk drive, is also provided for exporting data from the storage memory 56 or the programmer memory 54. The data storage unit 64 may be used to make backup copies of data stored in the programmer 32 or the implantable cardiac stimulating device 30.

An external printer 66 is used to print graphical or textual data at the user's request. An optional communication link 68 may be used to connect to a separate computer system, such as a hospital mainframe (not shown) or a dedicated PC database computer (not shown) for transferring data to and from the programmer 32. The communication link 68 may be a physical connection, or a remote connection such as an infrared, a radio frequency, or a cellular link.

A power source for the programmer 32 may be an on-board battery (not shown) or a power cord (not shown) connected to an electrical power outlet (not shown).

In accordance with the present invention, a transducer 70 is provided in order to receive voice commands from the user. The transducer 70 preferably converts audio signals to analog electrical signals. The transducer 70 preferably is a conventional microphone. An analog to digital (A/D) converter 72 preferably converts the analog electrical signals into digital data. In a preferred embodiment, the digital data from the A/D converter 72 are pre-processed by a digital signal processor (DSP) 74. The DSP 74 preferably provides the pre-processed digital data to the processing unit 52. The processing unit 52 preferably is implemented using a conventional voice recognition system, such as the Watson* BLASR Subword System, available from AT&T Advanced Speech Products Group, of Madison, Wis. (*Watson is a trademark of the AT&T Corp.) The voice recognition software preferably allows the programmer 32 to recognize voice commands. A list of voice commands which the programmer 32 is able to recognize preferably is stored in the memory 54 and/or the storage memory 56.

In a preferred embodiment, the programmer 32 is supplied to the user pre-programmed to recognize a predetermined list of commands. In one embodiment, the user is not able to add new voice commands to the programmer 32. In an alternative embodiment, however, the user may program the programmer 32 to recognize specific voice commands which are chosen by the user.

In an alternative embodiment (not shown), the digital data is fed directly from the A/D converter 72 to the processing unit 52. In this alternative embodiment, the pre-processing which would otherwise would be done by the DSP 74 is instead carried out by the processing unit 52. This alternate embodiment therefore eliminates the need for the DSP 74, but increases the processing burden on the processing unit 52. Voice recognition software which does not require the use of the DSP 74 includes, for example, Smartspeak*, available from Art Advanced Recognition Technologies, Inc., of Cupertino, Calif. (*Smartspeak is a trademark of Art Advanced Recognition Technologies, Inc.)

Figure 2:
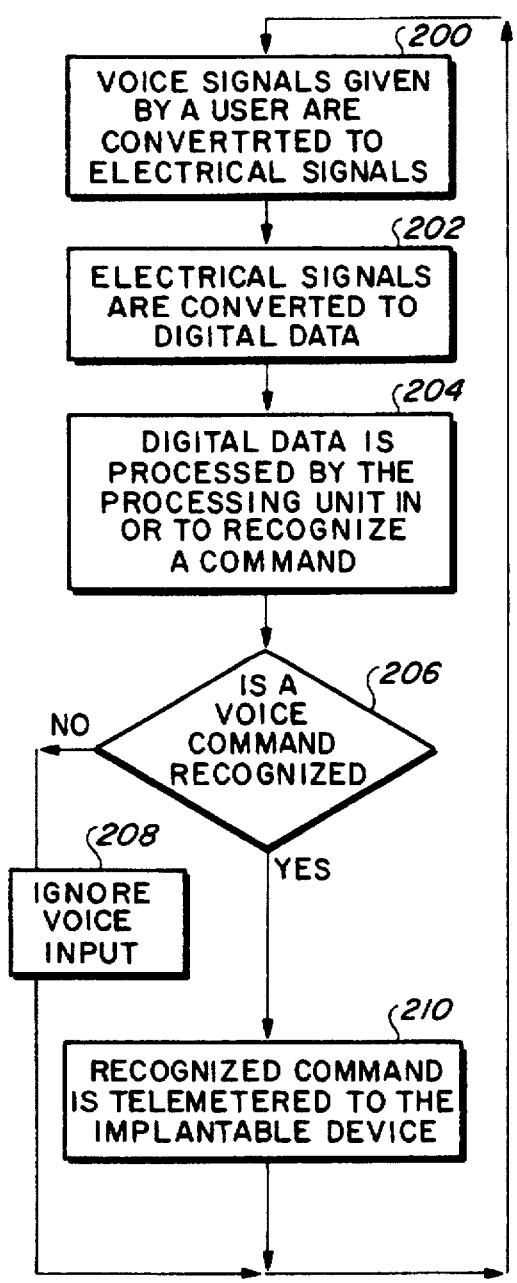
FIG. 2 is a flow diagram of the steps preferably carried out by the programmer-analyzer of FIG. 1 to control the implantable cardiac stimulating device using voice commands in accordance with the present invention.

The steps carried out by the programmer 32 in order to control the implantable cardiac stimulating device 30 using voice commands in accordance with a preferred embodiment of the present invention are shown in FIG. 2. The voice signals provided by the user preferably are converted into electrical signals by the transducer 70 (FIG. 1) at step 200. The electrical signals preferably are then converted into digital data by the A/D converter 72 (FIG. 1) at step 202. The digital data preferably are then processed by the processing unit 52 (FIG. 1) in order to recognize a command at step 204.

If a command is not recognized at test 206, the programmer 32 (FIG. 1) ignores the voice input at step 208. The programmer 32 (FIG. 1) may also generate an error message (not shown) if the voice command is not recognized at test 206. If a command is recognized at test 206, the programmer 32 (FIG. 1) telemeters the command to the implantable cardiac stimulating device 30 (FIG. 1) at step 210. Once the command has been telemetered to the device 30 (FIG. 1), the programmer 32 (FIG. 1) waits for further input from the user at step 200.

In accordance with the present invention, voice commands include, but are not limited to, commands which cause programs to be executed by the device 30 (FIG. 1), such as measuring the impedance of the lead 42 (FIG. 1), interrogating the program settings of the device 30 (FIG. 1), checking the status of the battery 50 (FIG. 1), and obtaining an AIEGM or VIEGM from the patient's heart. Voice commands also include commands which are used to program the device 30 (FIG. 1) and store data and historical information in the device 30 (FIG. 1). In general, any information or commands which can be manually entered via the user input device 62 (FIG. 1) can also be entered using voice commands.

Referring back to FIG. 1, in order to ensure that inappropriate commands are not inadvertently sent to the implantable cardiac stimulating device 30 by the programmer 32, the present invention preferably allows the user to confirm voice commands received by the programmer 32.

After a voice command has been spoken by the user and recognized by the programmer 32, the command preferably is communicated back to the user in order to allow the user to confirm the command. Once the command has been communicated to the user, the user may confirm the command, thereby causing the command to be telemetered to the implantable cardiac stimulating device 30 and then executed by the device 30 or, alternatively, the user may negate the command, thereby causing the command to be disregarded.

In a preferred embodiment, the command is communicated to the user through an audio output device 76. The audio output device 76 preferably communicates an audio signal which indicates the particular command. The audio signal preferably is a voice signal which corresponds to the particular command which the user has requested. A synthesized voice or a pre-recorded human voice may, for example, be used as the audio signal. The audio signal can, however, be an audio signal which does not correspond to a voice signal, such as an audible beep having a particular tone.

Once the audio signal has been communicated to the user via the audio output device 76, the user can then confirm the command by manually entering information through the user input device 62 or by voice command.

For purposes of illustration only, the following example is given. A user may recite the phrase, "return to standard." After recognizing the command, the programmer 32 then responds with the phrase "would you like to return to standard?" The user may then answer "yes" in order to cause this command to be carried out. Alternatively, the user may answer "no" if the user would not like the command to be carried out. Thus, a "yes" causes the command to be executed, while a "no" causes the command to be disregarded.

It will be clear to those skilled in the art that answers other than "yes" and "no" may be used. The programmer may for example respond with "affirmative" and "negative."

In another preferred embodiment, the command is displayed on the graphical display unit 58. The text or graphical figure which is displayed on the graphical display unit 58 indicates the particular command that the programmer has recognized. The user can then respond by speaking or by manually entering information through the user input device 62. The graphical display unit 58 preferably is located near the physician so that the physician can easily see the display.

For purposes of illustration only, the following example is given. The user may, for example, recite the phrase, "interrogate program settings." After the programmer 32 has recognized the command, the graphical display unit 58 displays the words "Interrogate program settings?" At this point, the user preferably may verbally answer either "yes" or "no." Alternatively, the user preferably may use the input device 62 to manually enter the response, for example, by pressing the appropriate location on the graphical display 58 using a digitizer-pen (not shown) to indicate whether or not the command should be executed.

Rather than displaying the words "Interrogate program settings?," a graphical figure such as an icon (not shown) appearing on the graphical display unit 58 can be highlighted. The user may then, for example, touch the icon with a digitizer-pen (not shown) in order to cause the command to be executed. The user may also speak the confirmation in order to cause the command to be executed.

In accordance with the present invention, both types of confirmation may be used simultaneously. The programmer 32 may display the command on the graphical display unit 58 and produce an audio signal which corresponds to the command. In accordance with the present invention the user may then confirm the command either by speaking the confirmation or by manually entering the confirmation through the user input device 62. The present invention thus allows the user to use the method which is most convenient under the particular circumstances.

In a preferred embodiment, the user is allowed to choose which of the above methods is used to confirm the command. The user preferably may choose whether to have the programmer provide an audio signal, graphical signal, or both of types of signals to indicate the recognized command. The user preferably may also choose whether to have the programmer recognize voice confirmation, manual confirmation, or both types of confirmation.

It is not necessary, however, that the user be able to choose which methods are used to indicate that a command has been recognized and to confirm the recognized command. It may be preferable in some cases to limit the choices available to the user. The user may be busy and not want to spend the time to set preferences such as what types of confirmation input will be accepted. It may be preferable in these and other situations to provide the programmer 32 to the user pre-programmed to accept a certain type of confirmation, or to limit the options available to the user in order to increase the simplicity and ease of use of the programmer 32.

It is preferable, although not necessary to practice the present invention, that a particular word be used to indicate to the programmer 32 that a command will follow. If such an "indicator word" is not used, the programmer 32 may respond to phrases taken out of context, or to phrases which were not intended for the programmer 32. The indicator word is used to alert the programmer 32 that a command is about to be given.

The indicator word may, for example, be a descriptive name such as "computer." For example, the user may say, "computer, run the test program." The word "computer" indicates to the programmer 32 that a command will follow. "Test program" is the particular command which the user is requesting. The indicator word also may be a phrase rather than a single word.

In addition to providing protection against commands being inadvertently carried out, the use of an indicator word eases the burden placed on the processing unit 52. This is true because the processing unit 52 need only look for the indicator word while it is waiting for a command. Preferably, only when the indicator word is detected does the processing unit 52 have to carry out the more involved task of comparing the voice input to a list of commands. Thus, during a large portion of time, the processing unit 52 is required only to compare the voice input to determine if it matches the indicator word, rather than a word or phrase chosen from the entire list of commands.

In a preferred embodiment, the user is allowed to choose whether or not an indicator word is used. It is not necessary, however, that the user decide whether or not to use an indicator word. The programmer 32 may be provided to the user pre-programmed with or without the use of an indicator word.

Figure 3:
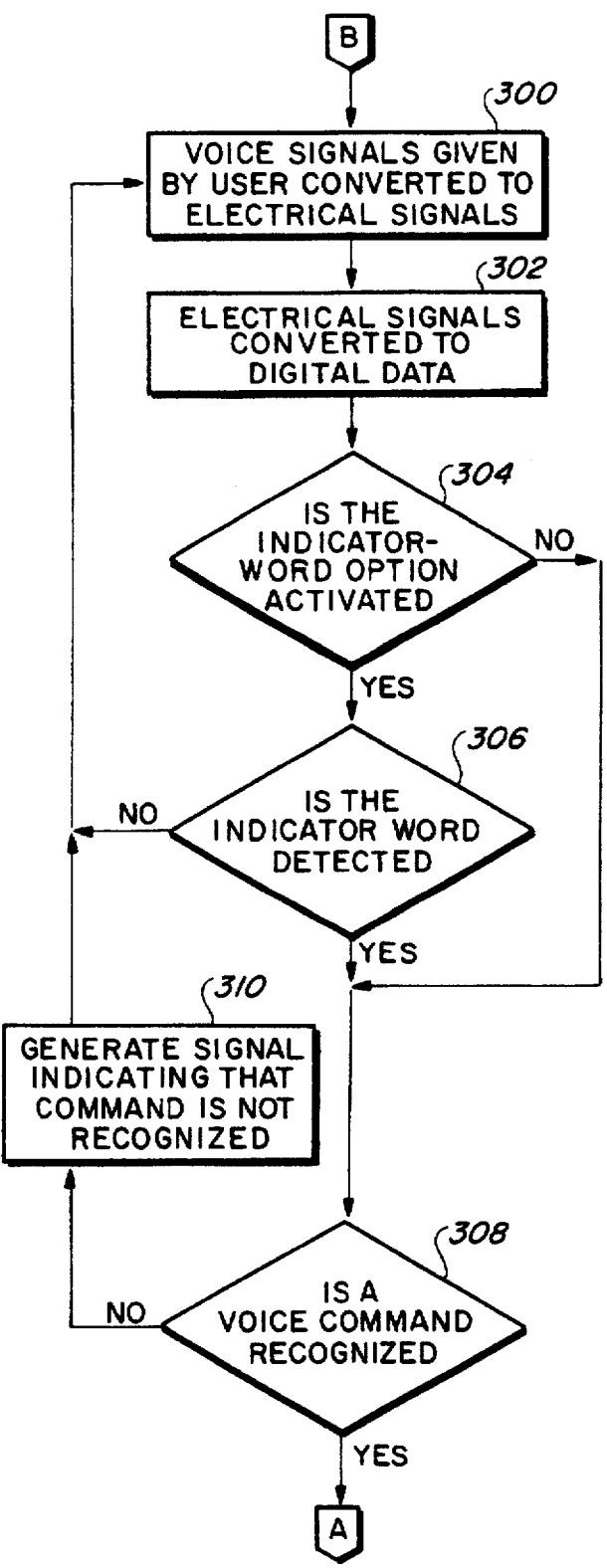
FIGS. 3 and 4 are flow diagrams of the steps preferably carried out by the programmer-analyzer of FIG. 1 to detect an indicator word and to allow a user to confirm a voice command in accordance with the present invention.
Figure 4:
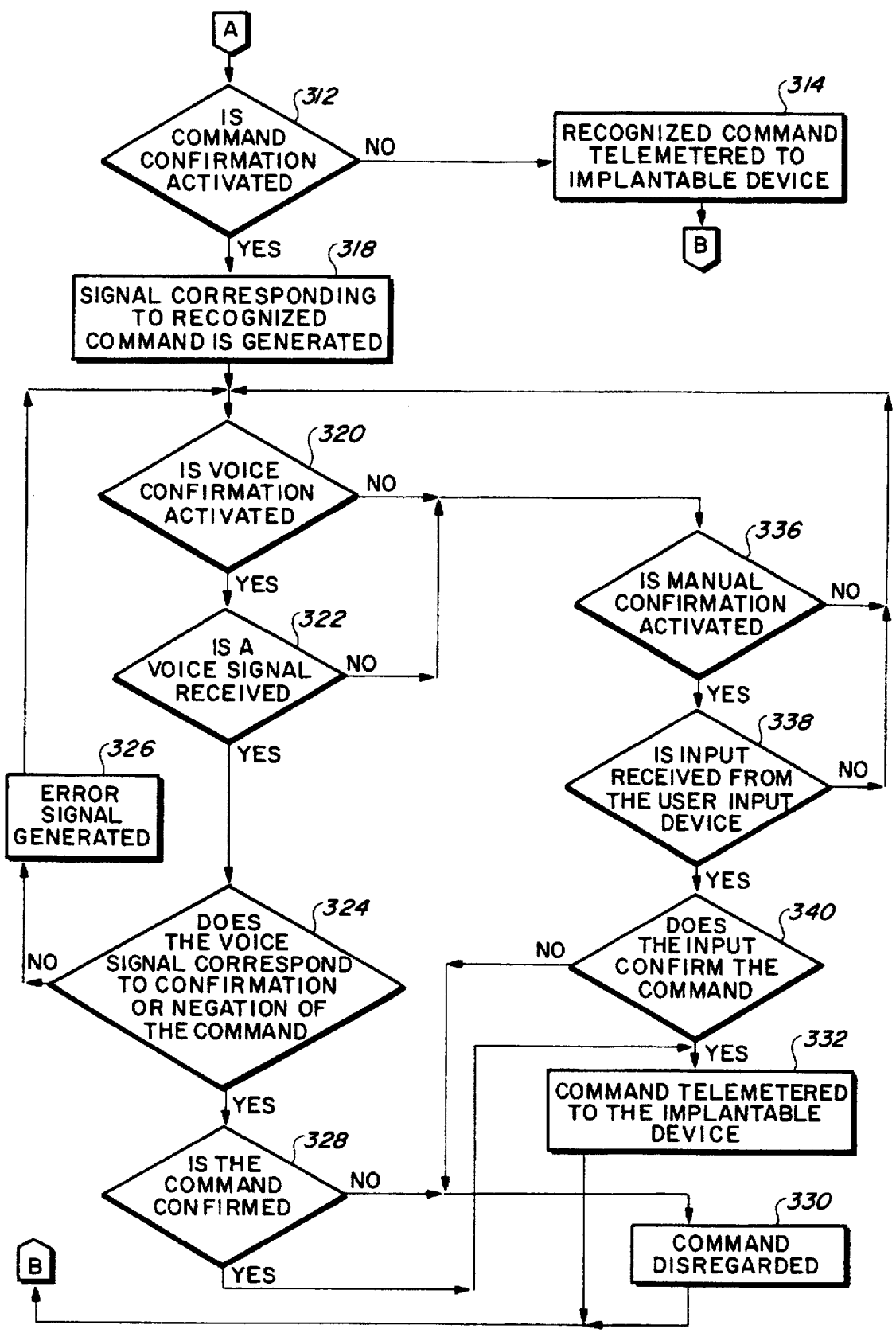

Reference is now made to FIGS. 3 and 4 which show the steps preferably carried out by the programmer 32 (FIG. 1) in order to recognize an indicator word and allow the user to confirm a command in accordance with the present invention. Referring first to FIG. 3, voice signals given by the user are converted to electrical signals at step 300. The electrical signals are converted into digital data by the A/D converter 72 (FIG. 1) at step 302. The programmer determines if the indicator-word option is activated at test 304. If the indicator-word option is activated at test 304, the programmer 32 (FIG. 1) determines if the indicator word has been detected at test 306. If the indicator word is not detected the programmer 32 (FIG. 1) returns to step 300 to wait for further input from the user.

If the indicator word is detected at test 306, the programmer 32 (FIG. 1) then analyzes the digital data in order to determine if a voice command is recognized at test 308. If the indicator-word option is not activated at test 304, the programmer 32 (FIG. 1) goes directly from test 304 to test 308 and determines if a voice command is recognized. If the digital data do not correspond to a command at test 308, the programmer 32 (FIG. 1) generates a signal which indicates to the user that the command is not understood at step 310. The programmer may, for example, indicate that a command is not understood by generating an audible signal with the audio output device 76 (FIG. 1), or by displaying a graphical message on the graphical display 58, or by generating both an audible massage and a graphical message.

Referring to FIG. 4, once a voice command is recognized by the programmer 32 (FIG. 1) at test 308, the programmer 32 (FIG. 1) determines if the command-confirmation option is activated at test 312. If the command-confirmation option is activated, the user is required to confirm the command recognized by the programmer 32 (FIG. 1).

If the command-confirmation option is not activated at test 312, the recognized command is telemetered to the implantable cardiac stimulating device 30 (FIG. 1) at step 314. Once the command is telemetered to the device, the programmer 32 (FIG. 1) preferably returns to step 300 (FIG. 3) to wait for further input from the user.

If the command confirmation option is activated, a signal corresponding to the recognized command is generated by the programmer 32 (FIG. 1) at step 318. The signal generated by the programmer 32 (FIG. 1) may be a graphical signal or an audible signal.

The programmer 32 (FIG. 1) determines if voice confirmation is activated at test 320. The user preferably may choose if the command may be confirmed by voice signal. If voice confirmation is activated, the programmer 32 (FIG. 1) determines if a voice signal is received at test 322. If a voice signal has been received, the programmer 32 (FIG. 1) determines if the voice signal corresponds to a confirmation or negation of the command at test 324. If the voice signal does not correspond to a confirmation or negation, the programmer 32 (FIG. 1) generates an error signal at step 326. The error signal preferably indicates to the user that the voice confirmation has not been understood, and preferably asks the user to repeat the confirmation or negation. The programmer 32 (FIG. 1) then returns to step 320 to wait for further input from the user.

If the voice signal corresponds to a confirmation or negation, the programmer then determines if the voice signal confirms the command at test 328. If the command is not confirmed, the programmer 32 (FIG. 1) disregards the command at step 330. If the command is confirmed, the command is transmitted to the implantable cardiac stimulating device 30 (FIG. 1) via the telemetry head 60 (FIG. 1) at step 332. After the command is either disregarded or telemetered to the device 30 (FIG. 1), the programmer 32 (FIG. 1) preferably returns to step 300 (FIG. 3) to wait for further input from the user.

Referring back to tests 320 and 322, if voice confirmation is not activated at test 320, or if a voice signal has not been received at test 322, the programmer 32 (FIG. 1) then determines if manual confirmation is activated at test 336. The user preferably is able to choose whether or not manual confirmation is activated. If manual confirmation is not activated, the programmer 32 (FIG. 1) returns to test 320. It is noted that at least one of manual confirmation and voice confirmation should be activated in order to allow the user to confirm the command. Accordingly, the programmer 32 (FIG. 1) preferably ensures that at least one type of confirmation is activated.

If manual confirmation is activated at test 336, the programmer 32 (FIG. 1) determines if input is received from the user input device 62 (FIG. 1) at test 338. If manual input has not been received from the user input device 62 (FIG. 1) at test 338, the programmer 32 (FIG. 1) then returns to test 320. If manual input has been received from the user input device 62 (FIG. 1) at test 338, the programmer 32 (FIG. 1) then determines if the manual input corresponds to confirmation of the command at test 340. If confirmation is received, the command is then transmitted to the implantable cardiac stimulating device 30 (FIG. 1) via the telemetry head 60 (FIG. 1) at step 332. If the command is not confirmed at test 340, the command is disregarded at step 330. After the command is either disregarded or telemetered to the device 30 (FIG. 1), the programmer 32 (FIG. 1) preferably returns to step 300 (FIG. 3).

Referring again to FIG. 1, although it is preferable to provide user confirmation of commands, there are certain situations in which it is preferable not to provide user confirmation. An example of such a situation is during certain parts of the procedure to implant the implantable cardiac stimulating device 30. During the implantation procedure, the physician usually tests the position of the lead 42 in the patient's heart by measuring the impedance of the lead 42. The physician may repeatedly move the lead and then measure the impedance. In order to test the position of the lead using voice commands, the physician preferably first gives a voice command to cause the programmer to enter the measurement mode. The physician may, for example, say, "enter measurement mode." After recognizing the command, the programmer 32 preferably asks the physician to confirm the command. Once the "enter measurement mode" command is confirmed the programmer 32 enters the measurement mode.

While the programmer 32 is in the measurement mode, confirmation preferably is not required. In order to measure the impedance of the lead 42, the physician preferably speaks the word "measure." After recognizing the command "measure," the programmer 32 preferably telemeters the command to measure the impedance of the lead 42 to the implantable cardiac stimulating device 30. The device 30 then preferably measures the impedance and then telemeters the results back to the programmer 32. Since the programmer 32 preferably does not require the user to confirm the command "measure," the physician is able to repeatedly position the lead 42 and its impedance with great ease. Rather than having to input commands into the user input device 62, the physicians hands are free to perform the implantation procedure. Once the lead has been positioned, the physician need only speak the word "measure" for the implantable cardiac stimulating device 30 to measure the lead impedance. The present invention thus eliminates the extra step of having an assistant enter the command and allows the physician to use his or her hands to perform medical procedure while controlling the programmer 32 through voice commands.

When the physician has completed the positioning of the lead and wants to exit the measurement mode, an exit command preferably is given. The exit command may, for example, be the word "exit."

Figure 5:
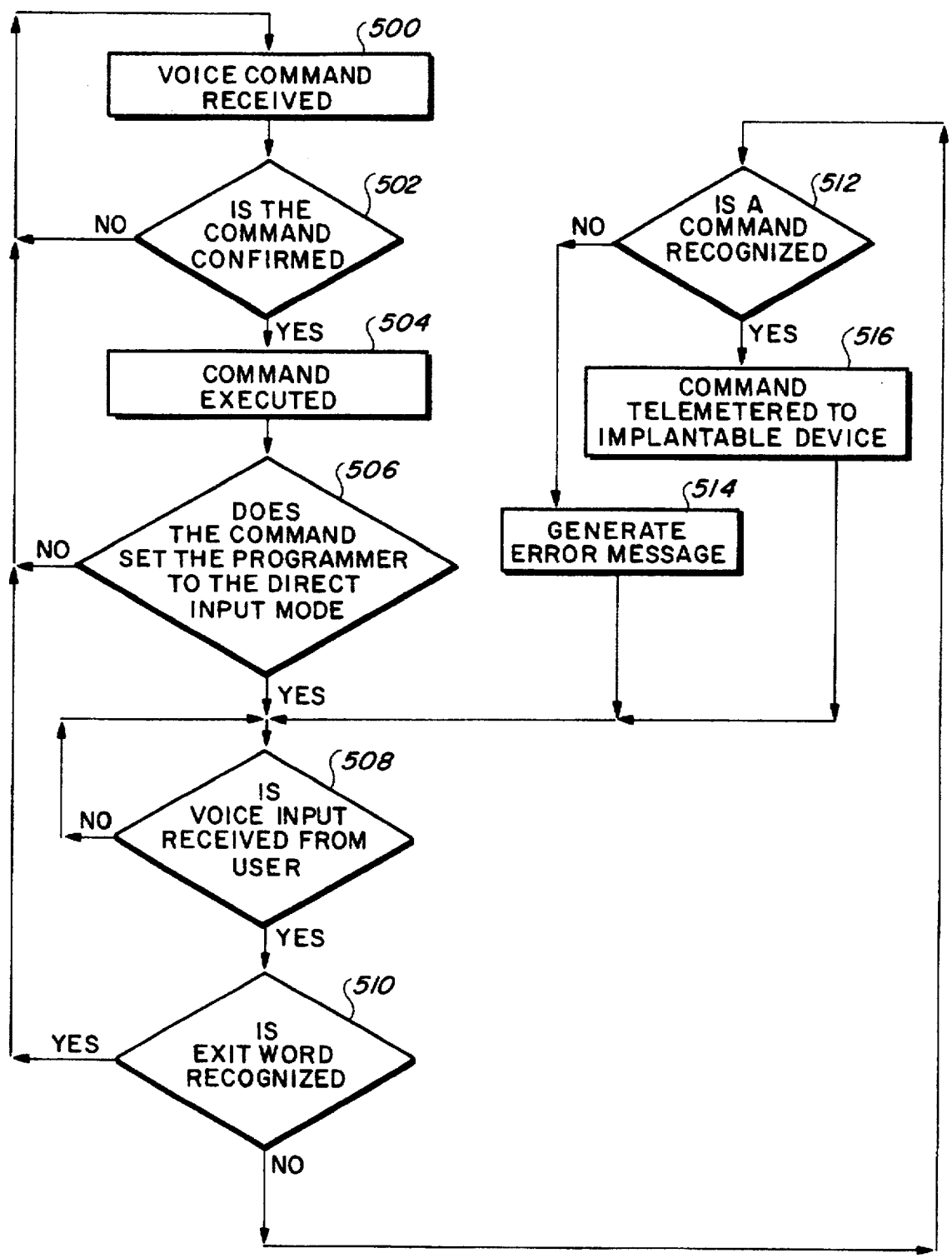
FIG. 5 is a flow diagram of the steps preferably carried out by the programmer-analyzer of FIG. 1 to allow a user to switch from a mode in which user confirmation is required to a mode in which user confirmation is not required.

A mode of the programmer 32 in which the user is able to input voice commands without having to provide confirmation is referred to herein as a "direct input" mode. The measurement mode preferably used for measuring the impedance of the lead 42 during the implantation procedure is an example of a direct input mode. A flow chart of the steps carried out by the programmer 32 to enter a direct input mode and execute voice commands is shown in FIG. 5.

A command is received and recognized by the programmer 32 (FIG. 1) at step 500. The programmer 32 (FIG. 1) then determines if the command is confirmed at step 502. If the command is not confirmed, the command is disregarded and the programmer 32 (FIG. 1) returns to step 500. If the command is confirmed at step 502, the programmer 32 (FIG. 1) then executes the command at step 504. The command executed at step 504 may be a command which is carried out only by the programmer 32 (FIG. 1) or it may be a command which is telemetered to the implantable cardiac stimulating device 30 (FIG. 1).

The programmer 32 (FIG. 1) checks to see if the command sets the programmer 32 (FIG. 1) to the direct input mode at test 506. If the command does not set the programmer 32 (FIG. 1) to the direct input mode, the programmer 32 (FIG. 1) then returns to step 500 to wait for further input from the user.

If the programmer 32 (FIG. 1) is put into the direct input mode at test 506, the programmer 32 (FIG. 1) waits for user input at test 508. If input is not received, the programmer 32 (FIG. 1) continues to wait for input at test 508. Once input has been received, the programmer 32 (FIG. 1) determines if the exit word has been detected at test 510. If the exit word is detected, the programmer 32 (FIG. 1) returns to step 500. If the exit word is not detected, the programmer 32 (FIG. 1) determines if the voice input corresponds to a command at test 512. If a command is not recognized at test 512, an error message is generated at step 514 which indicates to the user that the command has not been understood. The programmer then waits for further input from the user at step 508.

If the command is recognized at test 512, the programmer 32 (FIG. 1) telemeters the command to the implantable cardiac stimulating device 30 (FIG. 1) at step 516. The programmer then returns to step 508 in order to wait for further input from the user.

A preferred embodiment of the present invention thus allows the user to switch from a mode in which the user must confirm commands to a direct input mode in which the user can directly enter commands to the programmer 32 (FIG. 1) without having to confirm the command. Although the example given above with reference to the measurement of the impedance of the lead 42 (FIG. 1) describes a mode in which a single command (i.e., the "measure" command) is recognized and executed, multiple commands may be recognized in a direct input mode.

Referring back to FIG. 1, voice commands may be used in accordance with the present invention to execute any commands or functions of the implantable cardiac stimulating device 30. Examples of such commands include, but are not limited to, "return to standard" which returns the device 30 to the standard pacing mode, "emergency VVI" which puts the device into an emergency VVI mode, "program temporary settings" which allows the physician to set the device 30 to temporary settings for testing purposes, "revert to backup setting" which sets the device 30 to a backup pacing mode, and numerous other commands. Voice commands may also be used in accordance with the present invention to enter data into the implantable cardiac stimulating device 30, to program the implantable cardiac stimulating device 30, and to retrieve data, such as historical data, stored in the device 30.

It will be clear to those skilled in the art that the voice commands recognized by the programmer 32 may correspond to commands which may also be entered manually through the user input device 62. The user thus may choose to enter commands manually through the user input device 62 or simply by speaking the commands.

Thus, methods of and apparatus for controlling an implantable cardiac stimulating device using voice commands have been described. One skilled in the art will appreciate that the present invention can be practiced in other than the described embodiments, which are presented for the purpose of illustration rather than limitation, and the present invention is limited only by the claims which follow.

What is claimed is:

1. Apparatus for controlling an implantable medical device comprising:

processing means;

telemetry means coupled to the processing means for telemetrically communicating with the implantable medical device;

memory means coupled to the processing means for storing implantable device commands;

transducing means for converting audio signals into electrical signals; and analog to digital converter means coupled to the processing means and the transducing means for converting the electrical signals into digital data, wherein the digital data is processed by the processing means to determine if the digital data correspond to a command of the commands stored in the memory means, and wherein the telemetry means communicates a command which corresponds to the digital data to the implantable medical device when the digital data correspond to a command of the commands stored in the memory means.

2. The apparatus of claim 1, further comprising output means coupled to the processing means, wherein the matching command is communicated to a user of the apparatus using the output means, and wherein input is then received by the processing means from the user to allow the user to confirm the matching command, the matching command being communicated to the implantable medical device when the input from the user confirms the matching command.

3. The apparatus of claim 2, wherein the output means comprises graphical display means, and wherein the matching command is communicated to the user by graphically displaying the matching command on the graphical display means.

4. The apparatus of claim 3, wherein the matching command is represented as an icon on the graphical display means.

5. The apparatus of claim 2, wherein the output means comprises audio output means, and wherein the matching command is communicated to the user by an audio signal generated by the audio output means, the audio signal corresponding to the matching command.

6. The apparatus of claim 5, wherein the audio signal comprises an audio voice signal.

7. The apparatus of claim 2, wherein the input received from the user comprises voice input from the user.

8. The apparatus of claim 1, wherein the processing means processes the digital data to detect a predetermined word before processing the digital data to determine if the digital data correspond to any one of the plurality of commands, and wherein the digital data is processed to determine if the digital data correspond to any one of the plurality of commands only if the predetermined word is detected.

9. Apparatus for controlling an implantable medical device comprising:

processing means;

telemetry means coupled to the processing means for telemetrically communicating with the implantable medical device;

transducing means for converting audio signals given by a user into electrical signals;

analog to digital converter means coupled to the processing means and the transducing means for converting the electrical signals into digital data which are processed by the processing means to recognize voice commands, the processing means switching from a first mode of operation to a second mode of operation in response to a predetermined voice command; and output means for communicating information to the user, wherein:

while the processing means is in the first mode, a voice command given by the user and recognized by the processing means is communicated back to the user via the output means, and the user provides a predetermined voice confirmation to the transducing means in order to confirm the voice command and cause the voice command to be communicated to the implantable medical device via the telemetry means; and while the processing means is in the second mode, a voice command given by the user and recognized by the processing means is communicated to the implantable medical device via the telemetry means without allowing the user to confirm the voice command.

10. The apparatus of claim 9, wherein the output means comprises graphical display means, and wherein the voice command given by the user is communicated back to the user on the graphical display means.

11. The apparatus of claim 10, wherein the voice command given by the user is represented as an icon on the graphical display means.

12. The apparatus of claim 9, wherein the output means comprises audio output means, and wherein the voice command given by the user is communicated back to the user by an audio signal generated by the audio output means.

13. The apparatus of claim 12, wherein the audio signal comprises an audio voice signal.

14. A method of controlling an implantable medical device comprising the steps of:

receiving a voice command from a user;

converting the voice command into digital data;

processing the digital data to determine if the digital data correspond to any one of a plurality of implantable medical device commands; and transmitting a command which corresponds to the digital data to the implantable medical device using telemetry when the digital data correspond to any one of the plurality of implantable medical device commands.

15. The method of claim 14, further comprising the steps of:

communicating the command to a user before the transmitting step if the digital data correspond to any one of the plurality of commands; and receiving input from the user to allow the user to confirm the command, wherein the transmitting step comprises:
transmitting the command to the implantable medical device using telemetry if the input from the user confirms the command.

16. The method of claim 15, wherein the step of communicating the command to the user comprises visually displaying the command to the user.

17. The method of claim 16, wherein the step of visually displaying the command comprises displaying an icon.

18. The method of claim 15, wherein the step of communicating the command to the user comprises providing an audio signal which corresponds to the command.

19. The method of claim 18, wherein the audio signal comprises an audio voice signal.

20. The method of claim 15, wherein the step of receiving input from the user comprises receiving voice input from the user.

21. The method of claim 14, further comprising the step of processing the digital data to detect a predetermined word or phrase before the step of processing the digital data to determine if the digital data correspond to any one of the plurality of commands, wherein the steps of processing the digital data to determine if the digital data correspond to any one of the plurality of commands and transmitting the command are carried out only if the predetermined word is detected.

22. A method of operating a programmer for controlling an implantable medical device which receives voice commands from a user comprising the steps of:

providing a first mode of the programmer in which a voice command given by the user and recognized by the programmer is communicated back to the user by the programmer, and further in which the user provides a predetermined voice input to the programmer after the voice command has been communicated to the user in order to confirm the voice command and to cause the programmer to transmit the voice command to the implantable medical device;

providing a second mode of the programmer in which a voice command given by the user and recognized by the programmer is telemetered to the implantable cardiac stimulating device without allowing the user to confirm the voice command; and switching from the first mode to the second mode in response to receiving a predetermined voice command given by the user.

* * * * *